United States Patent
Cecala et al.

[11] Patent Number: 5,975,355
[45] Date of Patent: Nov. 2, 1999

[54] DOSAGE UNIT MEASURER FOR SYRINGE

[76] Inventors: Ann Cecala, 10115 W. Grand Ave., Melrose Park, Ill. 60164; Patricia Massey, 7813-C W. North Ave., River Forest, Ill. 60305

[21] Appl. No.: 08/882,488

[22] Filed: Jun. 25, 1997

[51] Int. Cl.⁶ ...................................................... B67D 5/22
[52] U.S. Cl. .......................... 222/43; 222/309; 222/283; 222/288
[58] Field of Search ............................ 222/309, 43, 283, 222/288

[56] References Cited

U.S. PATENT DOCUMENTS

| | | | |
|---|---|---|---|
| 2,233,554 | 3/1941 | Pletcher . | |
| 2,855,928 | 10/1958 | Reynolds | 222/43 |
| 3,730,389 | 5/1973 | Harris, Sr. et al. | 222/31 |
| 3,749,284 | 7/1973 | Kloehn | 222/43 |
| 4,248,225 | 2/1981 | Moore | 128/218 |
| 4,252,159 | 2/1981 | Maki | 141/27 |
| 4,267,846 | 5/1981 | Kontos | 128/765 |
| 4,444,335 | 4/1984 | Wood et al. | 222/43 |
| 4,489,766 | 12/1984 | Montada | 141/27 |
| 4,563,178 | 1/1986 | Santeramo | 604/208 |
| 4,874,385 | 10/1989 | Moran et al. | 604/208 |
| 5,009,645 | 4/1991 | Silver et al. | 604/207 |
| 5,344,409 | 9/1994 | Ennis, III et al. | 604/210 |

Primary Examiner—Andres Kashnikow
Assistant Examiner—David Deal
Attorney, Agent, or Firm—Gilhooly and Crossman

[57] ABSTRACT

A unit measurer for a syringe for use by the visually impaired or others including a plurality of blocks having predetermined lengths representing desired dosages. The blocks have a slot for individual placement on the rod of the syringe to limit movement of the syringe plunger for dispensing a given amount.

6 Claims, 1 Drawing Sheet

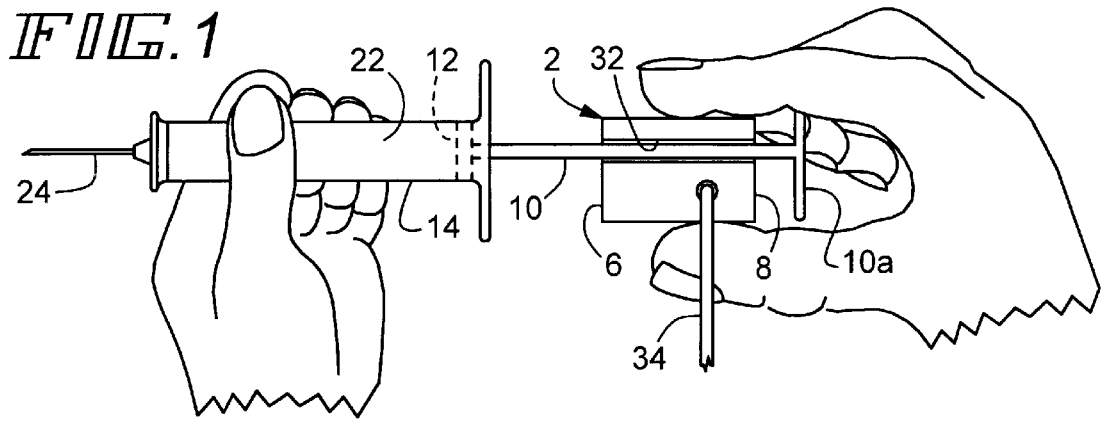
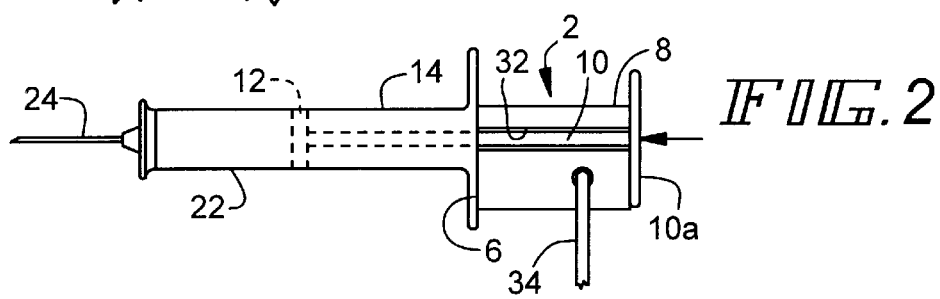
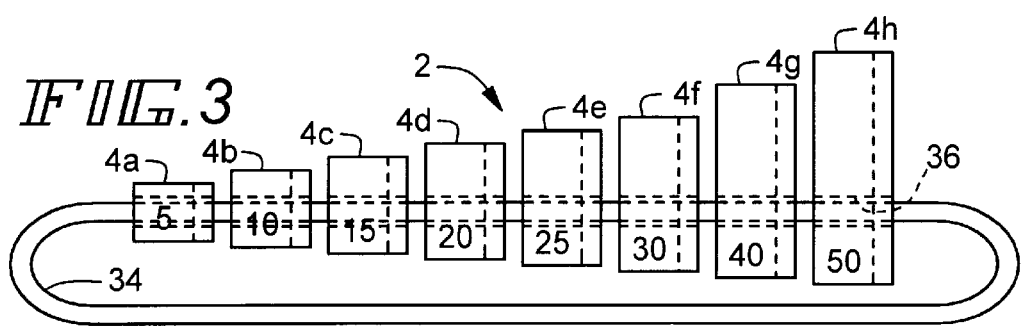
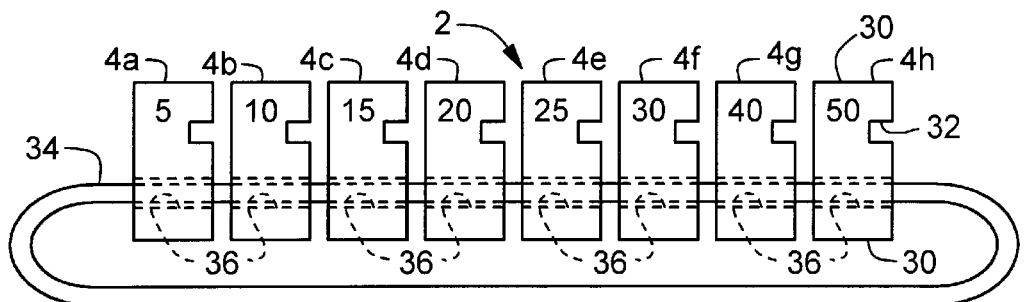
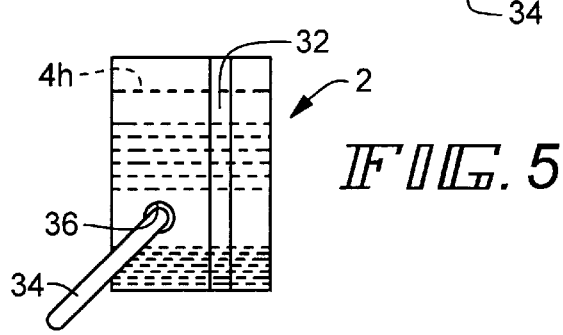

DOSAGE UNIT MEASURER FOR SYRINGE

BACKGROUND OF THE INVENTION

1. Field of the Invention

This invention relates in general to syringes and, in particular, to a measurer for dispensing accurate dosages from a syringe.

2. Summary of the Prior Art

Syringes are in common use for dispensing fluid into the body of an individual or animal. A syringe typically includes a cylindrical chamber or barrel having a plunger for ejecting a predetermined dosage through an extended hollow needle. The chamber may be calibrated by indicia to provide an external volume indication of the fluid in the barrel or chamber.

Conventional syringes are difficult to use by visually impaired individuals. A correct dosage is critical when administering medications, such as, insulin for diabetics. A visually impaired person may have great difficulty in accurately determining the volume of insulin or other medication in the syringe barrel. The use of an incorrect amount of medication can be harmful to the health of the individual who is self administering the dosage using a syringe.

Attempts to safely control the amount of fluid delivered by a syringe have not been satisfactory in the past. For example, the syringe disclosed in U.S. Pat. No. 3,749,284 employs a relatively complex calibrator strip assembly which is not practical for use by a visually impaired person. In U.S. Pat. No. 4,252,159, another complex dosage device is shown which controls the amount of medication withdrawn into the barrel before injection. Accordingly, it is desirable to provide an improved and safe technique by which a visually impaired individual can alone inject accurate dosages of medication with a syringe.

SUMMARY OF THE INVENTION

It is an objective of the invention to provide an accurate unit measurer for administering predetermined dosages of medication with a syringe, particularly useful to the visually impaired individual suffering from diabetes or other conditions. The invention herein disclosed includes a plurality of blocks having a respective length representing a predetermined volume of medication. Each block includes a slot arranged to be positioned on the external rod of the plunger of a conventional syringe. The block allows only a predetermined amount of movement of the plunger to dispense a predetermined volume of fluid. The visually impaired can easily use the invention and select a correct block by applying Braille indicia to the blocks or reading the information with a magnifying glass. The invention is simple to use and economical in design. Its effectiveness safeguards the health of the visually impaired and allows such individuals to self administer medications with ease.

BRIEF DESCRIPTION OF THE DRAWINGS

FIG. 1 is a side elevational view of one block of the unit measurer assembly of the invention being used in connection with a syringe by an individual;

FIG. 2 is a side elevational view of the one block of the unit measurer assembly used on the syringe of FIG. 1;

FIG. 3 is a side elevational view of the plurality of blocks of the unit measurer assembly of the invention retained on an optional ring;

FIG. 4 is a top plan view of the plurality of blocks of FIG. 3; and

FIG. 5 is an end elevational view of the block of FIG. 3.

DESCRIPTION OF THE PREFERRED EMBODIMENT

Referring now to FIGS. 1–5 there is illustrated the unit measurer assembly of the invention; generally designated by reference numeral 2. As seen in FIGS. 3–5, the unit measurer includes a plurality of blocks 4a–4h having a pair of flat parallel faces spaced a predetermined length between faces 6 and 8. The length of each block 4a–4h represents a range of dosages dependent on the length of the block. For example, the length of blocks may be selected to correspond to eight separate dosages having unit measurements of 5 to 50. The length of each block is determined to limit the stroke of the external rod 10 and plunger 12 of a conventional syringe 14 as will be apparent. The plunger 12 is conventionally mounted within barrel 22 to deliver medication through needle 24 previously withdrawn into the barrel. The length of each of the blocks 4a–4h is precisely selected so the amount of depression of the knob 10a of the rod 10 by an individual from a retracted position (FIG. 1) is limited by contact with opposite faces 6 and 8 of the particular block 4a–4h with knob 10 and the end of barrel 22 will deliver the selected volume after removal of the block from the syringe prior to injection. Thus, accurate doses can be injected from a full barrel 22 by expelling excess medication until the predetermined dosage is established by the particular block 4a–4h.

As seen in FIGS. 4 and 5, each block 4a–4h includes an open elongated slot 32 which is designed to fit on the external rod 10 of the plunger 12. By selecting the appropriate block 4a–4h having indicia designating volumetric doses, the slot 32 of the selected block is placed on the withdrawn rod 10 and is depressed by an amount determined by the length of the block. The blocks 4a–4h may be fabricated from any type of relatively rigid material, such as a plastic, metal or wood. For convenience each of the blocks 4a–4h may be retained on continuous ring 34 extending through holes 36 in the blocks 4a–4h as seen in FIGS. 3–5. Written indicia or Braille characters are applied to each block 4a–4h to indicate dosage levels. The invention of the application can be used by any individual, including the visually impaired.

In use of the invention for administering insulin, the plunger 12 may be pulled back to draw air into barrel 22. The needle 24 is inserted into an inverted insulin bottle (not shown) to fill the barrel with a predetermined amount of insulin. As seen in FIG. 1, one of the blocks 4a–4h representing a desired dosage is positioned on the rod 10 and the rod is depressed while the other hand is holding the syringe. Depression of the rod 10 will continue until faces 6 and 8 contact barrel 22 and knob 10a of a particular block 4a–4h after which the block is removed and the dosage in the syringe is injected into the patient.

What claim is:

1. A dosage unit measurer for a syringe for injecting a medication and having a barrel and extendable rod having an enlarged end and being attached to a plunger within the barrel moveable in opposite directions to respectively withdraw medication into the barrel and discharging medication from said barrel comprising block means having a pair of opposed external surfaces, respectively for contacting the enlarged end and the barrel, said pair of external surfaces being spaced by a length representing a predetermined dosage, said block means having attachment means for mounting said block means adjacent the extendable rod, said attachment means including an open slot extending between said pair of external surfaces; and said block means acting for arresting movement of the plunder within the barrel during discharge of medication at a position determined by said length between said external surfaces to establish said predetermined dosage in the barrel as said external surfaces respectively contact both the enlarged end and the barrel.

2. The dosage unit measurer according to claim 1 wherein said block means includes a pair of opposed flat, parallel faces.

3. The unit measurer according to claim 1 wherein said block means limits depression of the rod.

4. The unit measurer according to claim 1 wherein said block means includes a plurality of blocks, said blocks having varying length corresponding to different dosage volumes, one of said blocks being attached to extendable rod for a predetermined dosage.

5. The unit measurer according to claim 4 wherein said blocks include retention means for retaining the plurality of blocks, said retention means being a continuous ring.

6. The unit measurer according to claim 4 wherein each of said plurality of blocks includes indicia indicating dosage amount.

* * * * *